United States Patent
Crowe

(10) Patent No.: US 10,701,977 B2
(45) Date of Patent: Jul. 7, 2020

(54) PERMEABLE ELEMENT BASED VAPORIZATION PROCESS AND DEVICE

(71) Applicant: Vuber Technologies, Seattle, WA (US)

(72) Inventor: David Crowe, Lake Forest Park, WA (US)

(73) Assignee: Vuber Technologies, Inc., Seattle, WA (US)

( * ) Notice: Subject to any disclaimer, the term of this patent is extended or adjusted under 35 U.S.C. 154(b) by 0 days.

(21) Appl. No.: 15/860,641

(22) Filed: Jan. 2, 2018

(65) Prior Publication Data

US 2019/0200676 A1 Jul. 4, 2019

Related U.S. Application Data

(60) Provisional application No. 62/593,141, filed on Nov. 30, 2017, provisional application No. 62/543,316, filed on Aug. 9, 2017.

(51) Int. Cl.
| | |
|---|---|
| *A24F 13/00* | (2006.01) |
| *A24F 17/00* | (2006.01) |
| *A24F 25/00* | (2006.01) |
| *A24F 47/00* | (2020.01) |
| *H05B 3/06* | (2006.01) |
| *F22B 3/02* | (2006.01) |

(52) U.S. Cl.
CPC .............. *A24F 47/008* (2013.01); *F22B 3/02* (2013.01); *H05B 3/06* (2013.01)

(58) Field of Classification Search
CPC .................................................. A24F 47/008
USPC ................................................. 131/328, 329
See application file for complete search history.

(56) References Cited

U.S. PATENT DOCUMENTS

| | | | | |
|---|---|---|---|---|
| 5,954,979 | A * | 9/1999 | Counts .................. | A24F 47/008 131/194 |
| 8,678,012 | B2 * | 3/2014 | Li ......................... | A24F 47/008 128/202.21 |
| 8,973,585 | B2 * | 3/2015 | Goldstein .............. | B01D 53/14 131/173 |
| 2009/0260645 | A1 * | 10/2009 | Brotton ................ | A24B 15/246 131/342 |
| 2011/0094524 | A1 * | 4/2011 | Glover ..................... | A24F 1/30 131/224 |
| 2011/0226236 | A1 * | 9/2011 | Buchberger ...... | A61M 15/0021 128/200.23 |

(Continued)

*Primary Examiner* — Abdullah A Riyami
*Assistant Examiner* — Thang H Nguyen
(74) *Attorney, Agent, or Firm* — Alloy Patent Law; Walker Griffin Weitzel

(57) ABSTRACT

The present invention is a method for vaporizing concentrate that will substantially eliminate general or localized burning of concentrate during the vaporization process and a device adapted for carrying out said method. The vaporization method is based on heating concentrate that has been absorbed into a frit, preferably fitted glass. Fritted glass is characterized by open-pore interstices that allow free passage of fluid through the frit. It is commonly used as a filtering element, particularly in high-temperature applications. It was discovered that concentrate placed in contact with fitted glass is absorbed through capillary action. Although room temperature concentrate may not readily seep fully into fritted glass, as concentrate is heated its viscosity is reduced such that it is readily absorbed by the fitted glass.

6 Claims, 6 Drawing Sheets

(56) References Cited

U.S. PATENT DOCUMENTS

| | | | |
|---|---|---|---|
| 2013/0034739 A1* | 2/2013 | Boday | C09K 5/08 |
| | | | 428/447 |
| 2014/0238424 A1* | 8/2014 | Macko | A24F 47/008 |
| | | | 131/328 |
| 2016/0073695 A1* | 3/2016 | Sears | A24F 47/008 |
| | | | 131/329 |
| 2017/0197046 A1* | 7/2017 | Buchberger | A24F 40/44 |
| 2017/0224018 A1* | 8/2017 | Li | A24F 47/008 |
| 2017/0303587 A1* | 10/2017 | Johnson | H05B 1/0244 |
| 2017/0354186 A1* | 12/2017 | Johnson | A61M 11/042 |

* cited by examiner

PERMEABLE ELEMENT BASED VAPORIZATION PROCESS AND DEVICE

CROSS-REFERENCE TO RELATED APPLICATIONS

The present application is a nonprovisional application which claims the benefit of U.S. Provisional Applications 62/543,316 filed Aug. 9, 2017 entitled Vaporization Device and Process, and 62/593,141 filed Nov. 30, 2017 also entitled Vaporization Device and Process, which are both incorporated herein by reference in their entirety as if fully set forth herein.

FIELD OF THE DISCLOSURE

The overall field of invention is devices and methods for vaporization of liquids and solids.

BACKGROUND

*Cannabis* and tobacco have long been used recreationally and medicinally, with smoking being the traditional and prevalent means for consumption of both. A variety of other means for consumption currently exist, while new consumption means are continually being developed.

Vaporization has gained prevalence as a means for consumption. Vaporization differs from smoking in that the *cannabis* or tobacco, extracts thereof, or synthesized nicotine or cannabinoid concentrates are merely heated to the point of vaporization, rather than combusted. Vaporization ideally produces an inhalable vapor without producing smoke. Vaporization is a highly controllable process, wherein the amount of heating applied to either the plant or concentrate can be controlled precisely, and the size of the resulting dose of medicament is much more predictable than the size of a dose taken through smoking. Vaporization differs from smoking in that the raw plant or concentrate is heated to a temperature high enough to volatilize the medicament into vapor but low enough to avoid combustion. Combustion products and byproducts, such as smoke and $NO_R$, may be undesirable for consumption for a variety of reasons, including health effects and flavor preference. Vaporization optimally produces no smoke and the vapor will exhibit a complete absence of any associated burnt flavor.

Vaporizers adapted for use with concentrate typically rely on an ohmic resistive heating element that is either proximal to or in direct contact with the concentrate to be vaporized. Although the temperature and heat output of the heating element is controllable to some degree and is generally calibrated for a desired vapor production, the design inherently produces uneven heating of concentrate. This uneven heating creates some degree of micro localized concentrate burning with resulting smoke and associated burnt flavor. The presence of a burnt flavor can be exacerbated through improper vaporizer operation. Because smoke and burnt flavors are dominant and difficult to mask, even very small degrees of localized burning can produce a persistent burnt flavor.

A need exists for a vaporizer that is substantially resistant to producing smoke or any accompanying burnt flavor.

SUMMARY

The object of the present invention is to produce an improved concentrate vaporization method that is resistant to localized concentrate burning and an associated device adapted for performing said method.

The present invention is a method for vaporizing concentrate that will substantially eliminate general or localized burning of concentrate during the vaporization process and a device adapted for carrying out said method. The vaporization method is based on heating concentrate that has been absorbed into a frit, preferably fritted glass. Fritted glass is characterized by open-pore interstices that allow free passage of fluid through the frit. It is commonly used as a filtering element, particularly in high-temperature applications. It was discovered that concentrate placed in contact with fitted glass is absorbed through capillary action. Although room temperature concentrate may not readily seep fully into fitted glass, as concentrate is heated its viscosity is reduced such that it is readily absorbed by the fritted glass. While glass frits are preferred, other nonporous, heat-resistant materials, such as stainless steel, may be substituted for glass. Intrinsically porous materials, such as ceramic, are undesirable in this application, as it introduces uncontrolled pore sizes and geometries, which result in microscopic localized burning.

Frits have unusual thermal properties stemming from a combination of extremely high surface area relative to volume, permeability, porosity, high internal thermal resistivity due to relatively low conductive area between the individual sintered components that together comprise the frit. Frits differ from other porous solid filters in that they are formed by a sintering process in which a plurality of discrete particles are fused through application of heat and pressure. Unexpectedly, when a frit has absorbed concentrate, the frit may be directly exposed to heat sources, including flame or radiant heat, and concentrate contained within the frit will be heated sufficiently to vaporize, but insufficiently to cause any substantial localized burning. Additionally, frits are themselves filters, and micron filter frits, when used in this application, provide the particulate filtration that further improves the quality of produced vapor over traditional vaporization methods.

The invented method of vaporization is therefore to cause a frit to absorb concentrate, to heat said frit and contained concentrate sufficiently to produce vapor while producing extremely limited localized burning to the extent that any associated burnt flavor would be essentially undetectable by the human palate, and to evacuate said vapor.

The invented device is a vaporizer specially adapted to carry out the invented method.

DEFINITIONS

Figure 1:
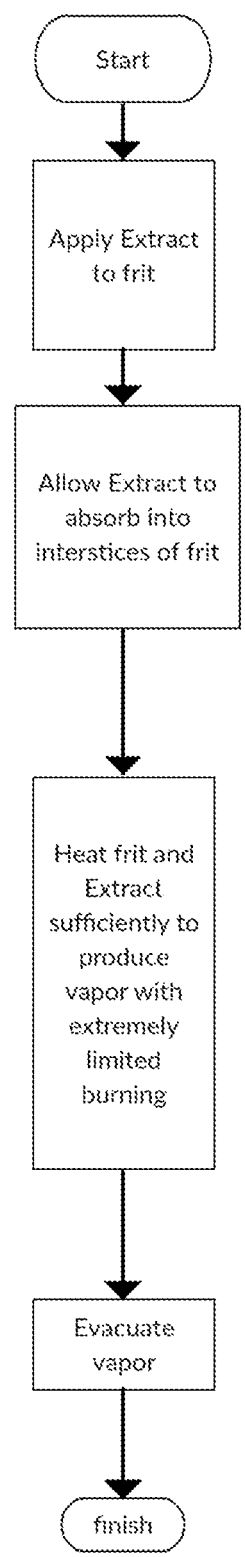
FIG. 1 Shows a flow diagram of the method.

Vapor: Gaseous or suspended liquid condensate suitable for inhalation.

Vaporize: to produce vapor from a liquid or solid.

Vaporizer: Device used to vaporize.

Sinter: To fuse constituent solid components into a single solid component through application of heat and pressure.

Glass: any solid comprised mostly of vitreous silica.

Quartz glass: glass comprised of chemically pure vitreous silica.

Frit: Permeable vaporization element such as s Sintered glass filter or sintered filter of any intrinsically non-porous and heat-resistant composition (for example, stainless steel) that is substituted where a frit of glass may otherwise have been used.

Concentrate: Formulation of extracted active ingredients from *Cannabis* or

Tobacco, including cannabinoids such as THC or CBD, alkaloids such as nicotine, or other medicinal or psychoactive compounds, or synthetic versions thereof. Generically, this includes cannabinoid extracts such as oil, wax, budder, shatter, and similar products, as well as nicotine products such as e-juice and similar products.

DETAILED DESCRIPTION

In the Summary above, Detailed Description, claims below, and accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limits include both numbers. For example, "25 to 100" means a range whose lower limit is 25 and upper limit is 100, and includes both 25 and 100.

FIG. 1 shows a flow diagram of the invented method, comprised of four steps.

Step 1: Apply concentrate to a frit. In the preferred method, said frit is a fitted glass disc.

Step 2: Allow concentrate to absorb into interstices of said frit, preferably through application of heat to said concentrate and frit. In the preferred method, heat is applied via radiant heating from a proximal ohmic resistive heating element. In alternative methods, other heat sources may be used including flame or high-temperature air or other gas.

Step 3: Continue heat application to induce vaporization of said concentrate to produce a vapor.

Step 4: Evacuate said vapor.

Figure 2:
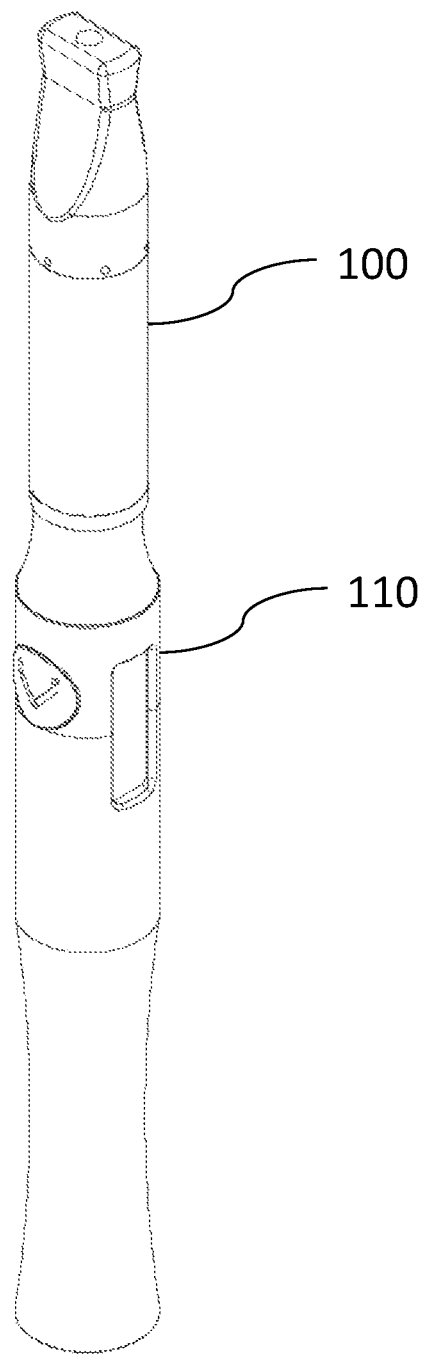
FIG. 2 Shows an isometric view of the vaporizer.

FIG. 2 is an isometric view of the vaporizer, which is adapted for performing the invented method. The vaporizer is comprised of an atomizer 100, and a battery 110 adapted to supply electrical current to the atomizer 100.

Figure 3:
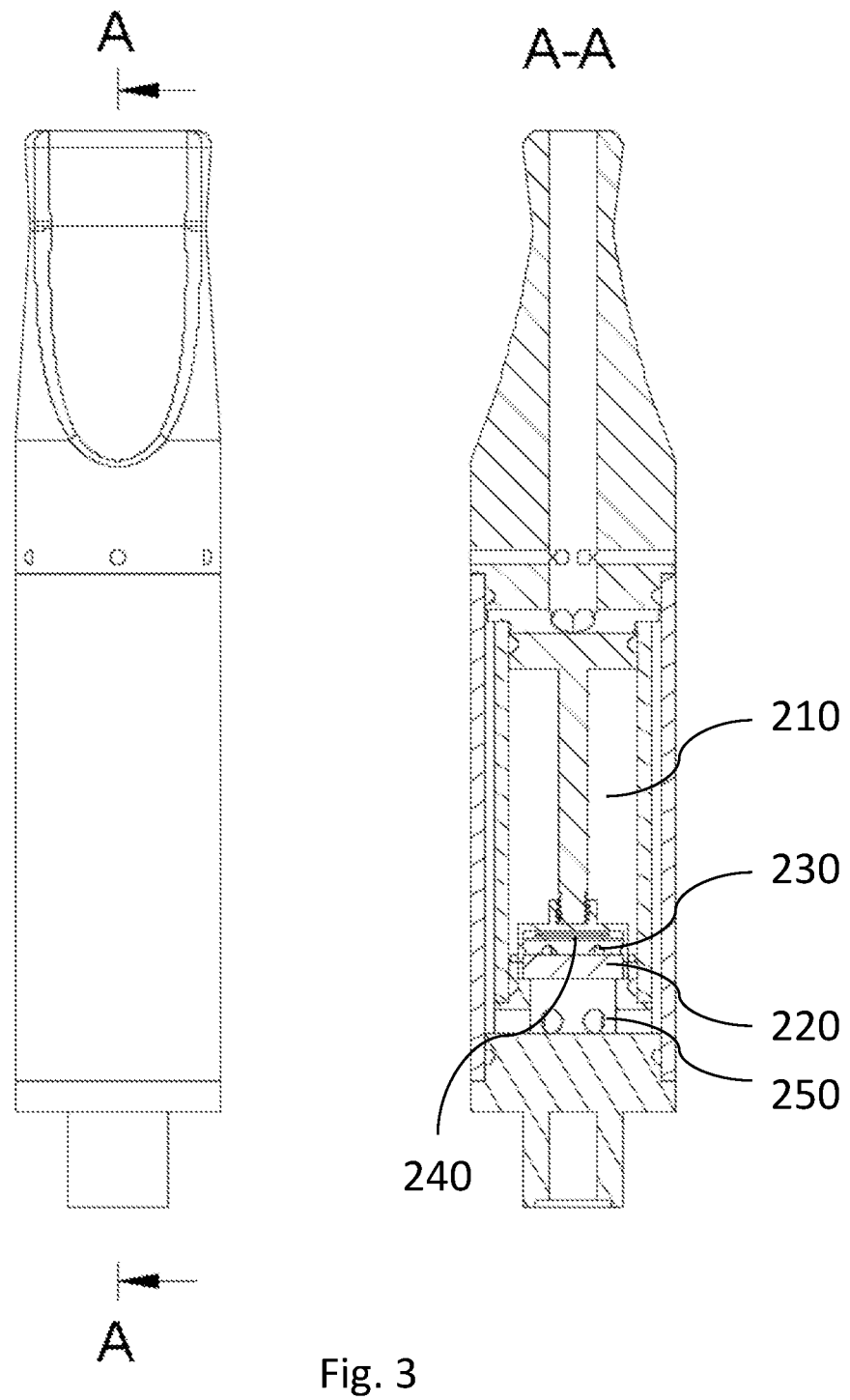
FIG. 3 Shows front and section views of the atomizer.

FIG. 3 is a front view and section view of the atomizer 100. The atomizer is comprised of a concentrate reservoir volume 210 capable of containing some volume of concentrate, a frit 220, a supply port 230 through which concentrate may flow from the reservoir volume 210 to the frit 220, a heat source 240 proximal to the frit 220, and an evacuation channel 250.

Figure 4:
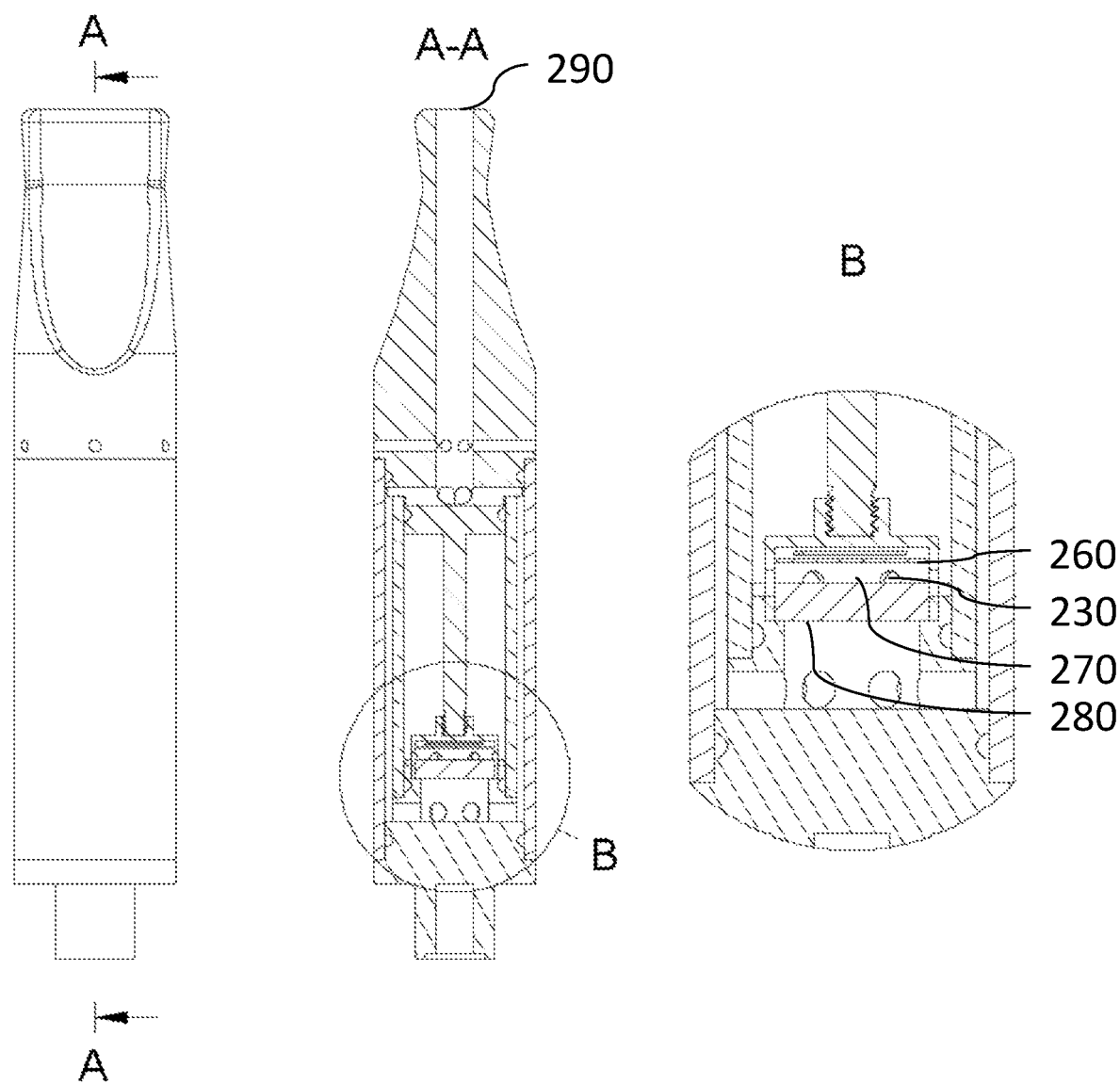
FIG. 4 Shows front and section views of the atomizer and a detail view of the frit and proximal components.

FIG. 4 Shows front and section views of the atomizer and a detail view of the frit 220 and proximal components. In the preferred embodiment, the supply ports 230 are positioned such that concentrate freely flows to a concentrate preheating chamber 270. In the preferred embodiment, the preheating chamber 270 is a cylindrical reservoir volume formed by the frit 220 on its lower face, and the heating element 240 at its upper face. When the heat source 240 is operated, concentrate contained within the preheating chamber 270 will increase in temperature with a resulting reduction in viscosity. The reduced viscosity allows the concentrate to be readily absorbed into the interstices of the frit 220.

Figure 5:
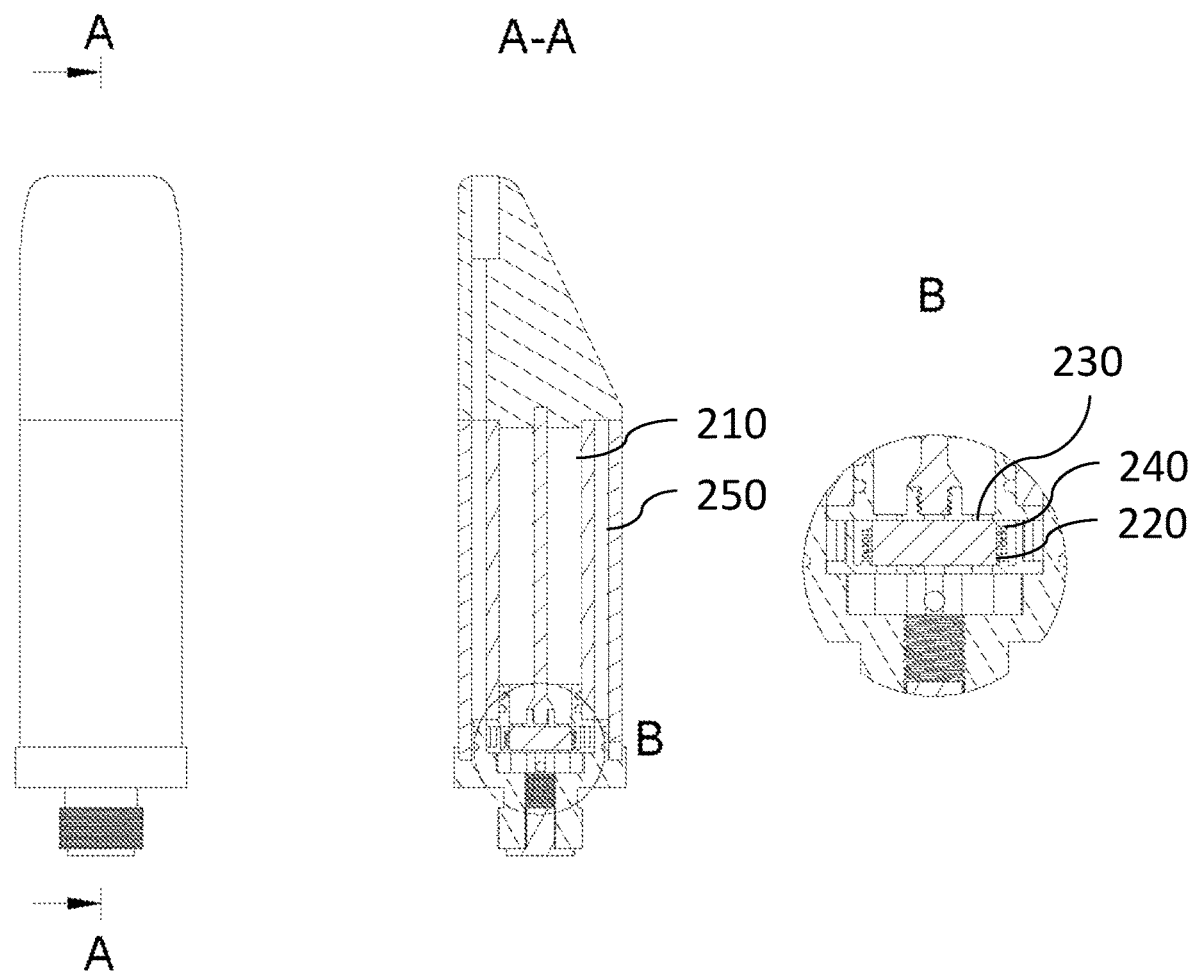
FIG. 5 Shows front and section views of an alternative embodiment of the atomizer and a detail view of the frit and proximal components.

FIG. 5 shows an embodiment of the atomizer. In this embodiment, the heating element 240 is a helical resistive element that is positioned proximally and coaxially with the frit 220. In the embodiment, the supply port 230 is in direct fluid communication with the fit 220. As concentrate is vaporized and evacuated through the evacuation channel 250, concentrate will be flow from the reservoir volume 210 into the frit until the frit 220 and resaturated it with concentrate.

In the preferred embodiment, the heating source 240 is an ohmic heating element, which produces heat when electrical current is supplied. In the preferred embodiment, the heating element 240 is a coil, captured by a glass plate 260. In alternative embodiments, the heating element 240 may be potted, freely exposed within the preheating chamber 270, embedded within preheating chamber 270 walls, embedded within the frit 220, or otherwise positioned proximal to or in contact with the frit 220 such that heat output from the heating element 240 is transferred to the frit 220. In alternative embodiments, the heat source 240 may be a flame or other heat source. The heating element in the preferred embodiment is operable by a user through user control of the electrical current. In the preferred embodiment, the attached battery 110 will control current to the heat source 240, typically through a switch, in order to supply electrical current to the heating element. The heating element will produce heat, which is transferred to the frit and any absorbed concentrate. The heated concentrate will vaporize. Vaporized concentrate will freely flow through the frit 210 and exit through the frit lower surface 280 into the evacuation channel 250. The resulting vapor may be evacuated from the device through the evacuation channel 250 by means of application of a pressure differential, said pressure differential typically produced by a user inhaling through the evacuation channel 250 at the egress port 290.

As concentrate contained within the frit 220 is vaporized, gravity and capillary action will cause concentrate to flow from the concentrate reservoir 210 through the supply port 230 to resaturate the frit 220. Resaturation is aided by preheating concentrate contained in the preheating chamber 270. Resaturation of the frit 220 is further aided by the arrangement of the heating element 240, the preheating chamber 270, and the frit 210.

Figure 6:
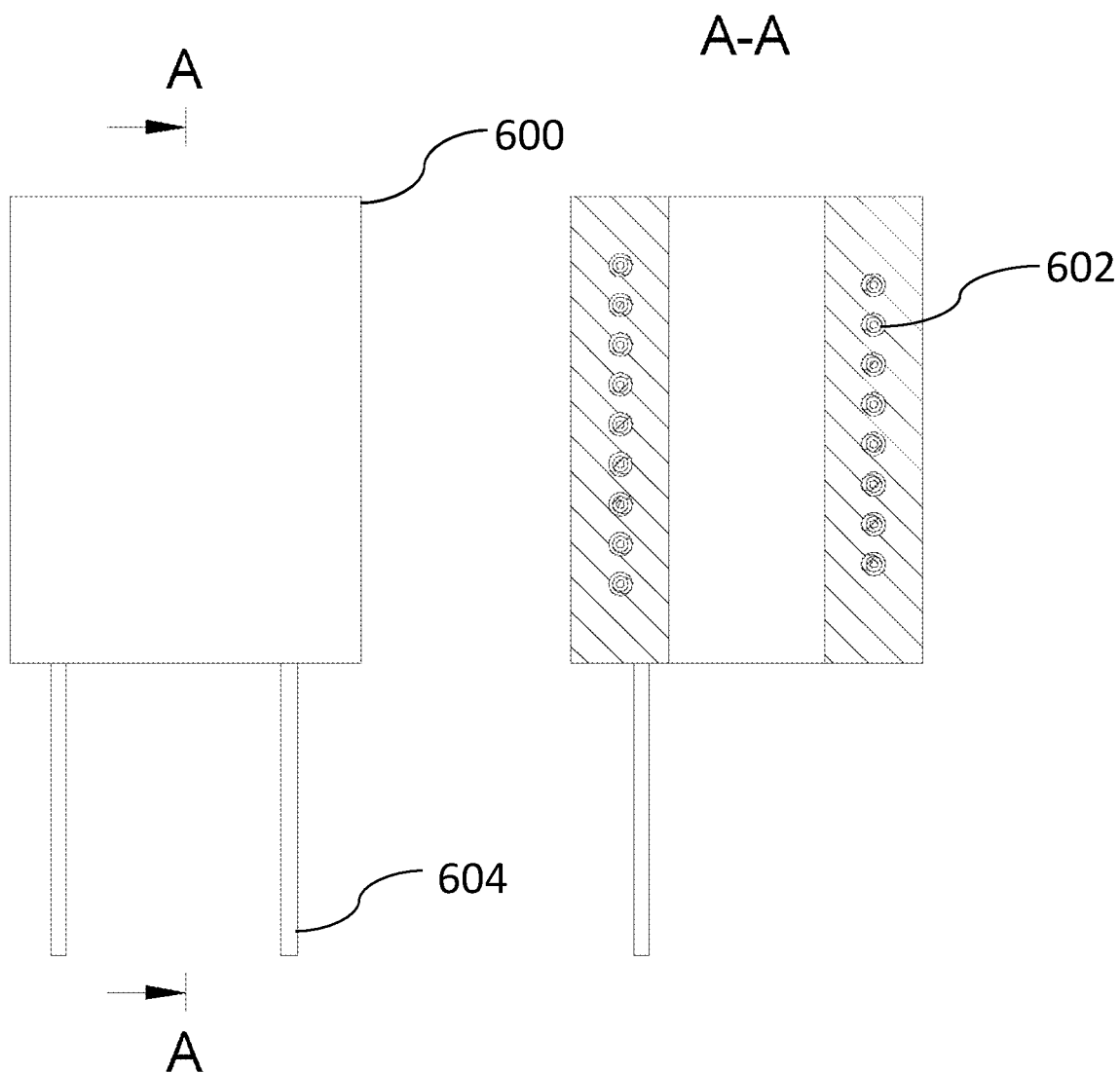
FIG. 6 Shows front and section views of an alternative embodiment of the frit having an embedded heating element.

FIG. 6 Shows front and section views of an alternative embodiment of the frit having an embedded heating element. In the embodiment, the frit 600 is generally cylindrical. The heating element 602 has leads 604 that, when connected to the cathode and anode of a battery, form an electric circuit. The heating element 602 is embedded within the volume of the frit 600.

PREFERRED METHOD OF USE

In the preferred method of use, the concentrate is of sufficiently low viscosity that it will readily flow toward gravity. The heating element 240 is activated by user control of a switch on the battery 110, which will cause concentrate contained within the frit 220 to vaporize, and the user will inhale resulting vapor by inhaling at the egress port 290 of the evacuation channel 250.

While preferred and alternate embodiments have been illustrated and described, as noted above, many changes can be made without departing from the spirit and scope of this VAPORIZATION PROCESS AND DEVICE. Accordingly, the scope is not limited by the disclosure of these preferred and alternate embodiments. Instead, the scope of the VAPORIZATION PROCESS AND DEVICE is to be determined entirely by reference to the claims. Insofar as the description above and the accompanying drawings (if any) disclose any additional subject matter that is not within the scope of the claims below, the inventions are not dedicated to the public and Applicant hereby reserves the right to file one or more applications to claim such additional inventions.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example of a generic series of equivalent or similar features.

Any element in a claim that does not explicitly state "means for" performing a specified function, or "step for" performing a specific function is not to be interpreted as a "means" or "step" clause as specified in 35. U.S.C. § 112 ¶6. In particular, the use of "step of" in the claims herein is not intended to invoke the provisions of U.S.C. § 112 ¶6.

I claim:

1. A vaporization device comprising:
   a concentrate supply reservoir in fluid communication with a concentrate vaporization assembly, said concentrate vaporization assembly comprising:
   a frit filter adapted to absorb concentrate from said supply reservoir, and
   a resistive heating element proximal to said frit filter, and adapted to heat said frit filter and absorbed concentrate; and
   a vapor collection and discharge assembly comprising:
   a vapor accumulation chamber in fluid communication with said frit filter, and
   a vapor evacuation channel in fluid communication with said vapor accumulation chamber and in fluid communication with an egress port.

2. The device of claim 1, wherein the frit filter is sintered glass.

3. The device of claim 1, wherein the resistive heating element is embedded within the frit filter.

4. The device of claim 2, wherein the frit filter is sintered quartz glass.

5. A vaporization process comprising:
   concentrate being applied to a surface of a frit filter,
   allowing said frit filter to absorb said concentrate through capillary action,
   using an ohmic resistance heater to heat said frit filter and contained concentrate sufficiently to produce a vapor of said concentrate.

6. The vaporization process of claim 5 wherein said frit filter absorption of said concentrate through capillary action is induced by reduction of concentrate viscosity through application of heat to said concentrate.

\* \* \* \* \*